US009125905B2

(12) United States Patent
Calderari et al.

(10) Patent No.: US 9,125,905 B2
(45) Date of Patent: *Sep. 8, 2015

(54) LIQUID PHARMACEUTICAL FORMULATIONS OF PALONOSETRON

(71) Applicants: Helsinn Healthcare SA, Lugano/Pazzallo (CH); Roche Palo Alto LLC, Palo Alto, CA (US); Simone Macciocchi, Melide (CH); Giulio Macciocchi, Breganzona (CH)

(72) Inventors: Giorgio Calderari, Rancate (CH); Daniele Bonadeo, Casalzuigno (IT); Roberta Cannella, Varese (IT); Alberto Macciocchi, Melide (CH); Andrew Miksztal, Palo Alto, CA (US); Thomas Malefyt, Carmel Valley, CA (US); Kathleen M Lee, Palo Alto, CA (US)

(73) Assignees: Helsinn Healthcare SA, Lugano/Pazzallo (CH); Roche Palo Alto LLC, Palo Alto, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/597,489

(22) Filed: Jan. 15, 2015

(65) Prior Publication Data

US 2015/0141454 A1 May 21, 2015

Related U.S. Application Data

(63) Continuation of application No. 13/902,299, filed on May 24, 2013, which is a continuation of application No. 13/901,437, filed on May 23, 2013, now Pat. No. 8,598,219, which is a continuation-in-part of application No. 13/087,012, filed on Apr. 14, 2011, now Pat. No. 8,518,981, which is a continuation of application No. 11/186,311, filed on Jul. 21, 2005, now Pat. No. 7,947,724, which is a continuation of application No. PCT/EP2004/000888, filed on Jan. 30, 2004.

(60) Provisional application No. 60/444,351, filed on Jan. 30, 2003.

(51) Int. Cl.
*A61K 31/47* (2006.01)
*A61K 47/26* (2006.01)
*A61K 31/473* (2006.01)
*B65B 55/02* (2006.01)
*B65B 7/16* (2006.01)

(52) U.S. Cl.
CPC .................. *A61K 31/473* (2013.01); *B65B 7/16* (2013.01); *B65B 55/02* (2013.01)

(58) Field of Classification Search
USPC ................................................. 514/296, 397
See application file for complete search history.

(56) References Cited

U.S. PATENT DOCUMENTS

| | | | |
|---|---|---|---|
| 4,695,578 A | 9/1987 | Coates et al. |
| 4,753,789 A | 6/1988 | Tyers et al. |
| 4,886,808 A | 12/1989 | King |
| 4,906,755 A | 3/1990 | Gittos |
| 4,929,632 A | 5/1990 | Tyers et al. |
| 4,937,247 A | 6/1990 | King |
| 5,011,846 A | 4/1991 | Gittos et al. |
| 5,034,398 A | 7/1991 | King |
| 5,202,333 A | 4/1993 | Berger et al. |
| 5,240,954 A | 8/1993 | Tyers et al. |
| 5,272,137 A | 12/1993 | Blase et al. |
| 5,344,658 A | 9/1994 | Collin |
| 5,578,628 A | 11/1996 | Tyers et al. |
| 5,578,632 A | 11/1996 | Tyers et al. |
| 5,622,720 A | 4/1997 | Collin |
| 5,854,270 A | 12/1998 | Gambhir |
| 5,922,749 A | 7/1999 | Tyers et al. |
| 5,955,488 A | 9/1999 | Winterborn |
| 6,063,802 A | 5/2000 | Winterborn |
| 6,132,758 A | 10/2000 | Munayyer et al. |
| 6,284,749 B1 | 9/2001 | Castillo et al. |
| 6,287,592 B1 | 9/2001 | Dickinson |
| 6,294,548 B1 | 9/2001 | James |
| 6,699,852 B2 | 3/2004 | Robichaud |
| 7,109,339 B2 | 9/2006 | Lee et al. |
| 7,947,724 B2 | 5/2011 | Calderari et al. |
| 7,947,725 B2 | 5/2011 | Calderari et al. |
| 7,960,424 B2 | 6/2011 | Calderari et al. |
| 8,518,981 B2 | 8/2013 | Calderari et al. |
| 8,598,218 B2 | 12/2013 | Calderari et al. |

(Continued)

FOREIGN PATENT DOCUMENTS

EP     0 512 400 A1    4/1992
WO    WO-03100091    12/2003

(Continued)

OTHER PUBLICATIONS

R. M. Eglen et al., "Pharmacological characterization of RS 25259-197, a novel and selective 5-HT3 receptor antagonist, in vivo," Br. J Pharmacology 114:860-866 (1995).

Chelly, Jacques et al., Oral RS-25259 Prevents Postoperative Nausea and Vomiting Following Laparoscopic Surgery, Anesthesiology, 1996, vol., 85, No. 3A, p. A21.

Sorbe, Bengt, 5-HT-3 Receptor Antagonists as Antiemetic Agents in Cancer Chemotherapy, extracted from Expert Opinion on Investigational Drugs, 1996, vol. 5 No. 4, pp. 389-407.

(Continued)

*Primary Examiner* — Shirley V Gembeh
(74) *Attorney, Agent, or Firm* — Clark G. Sullivan; Troutman Sanders LLP

(57) ABSTRACT

The present invention relates to shelf-stable liquid formulations of palonosetron for reducing chemotherapy and radiotherapy induced emesis with palonosetron. The formulations are particularly useful in the preparation of intravenous and oral liquid medicaments.

9 Claims, No Drawings

(56) References Cited

U.S. PATENT DOCUMENTS

| | | | |
|---|---|---|---|
| 8,598,219 | B2 | 12/2013 | Calderari et al. |
| 8,729,094 | B2 | 5/2014 | Calderari et al. |
| 2001/0020029 | A1 | 9/2001 | James |
| 2003/0095926 | A1 | 5/2003 | Dugger, III |
| 2004/0147510 | A1 | 7/2004 | Landau et al. |
| 2013/0261149 | A1 | 10/2013 | Calderari et al. |
| 2013/0261150 | A1 | 10/2013 | Calderari et al. |
| 2013/0289065 | A1 | 10/2013 | Calderari et al. |
| 2014/0039000 | A1 | 2/2014 | Calderari et al. |

FOREIGN PATENT DOCUMENTS

| | | |
|---|---|---|
| WO | WO-2004045615 | 6/2004 |
| WO | WO-2004067005 | 8/2004 |
| WO | WO-2004073714 | 9/2004 |

OTHER PUBLICATIONS

Gaster, Laramie M. and King, Frank D., Serotonin 5-HT3 and 5-HT4 Receptor Antagonists, extracted from Medicinal Research Reviews, 1997 vol. 17, No. 2, pp. 163-214.

Tang, Jun et al., "Efficacy of RS-25259, a Novel 5-HT3 Antagonist, In the Prevention of Postoperative Nausea and Vomiting after Major Gynecologic Surgery," Anesthesiology, 1997, vol. 85, No. 3 suppl. p. A329.

Tang, Jun et al., The Efficacy of RS-25259, a Long-Acting Selective 5-HT3 Receptor Antagonist, for Preventing Postoperative Nausea and Vomiting After Hysterectomy Procedures, Anesthesia and Analgesia, 1998, vol. 87, pp. 462-467.

Adis R&D Profile, Palonosetron RS 25259 197, Drugs in R&D, Oct. 1999, vol. 2, No. 4, pp. 251-252.

Piraccini Gaia et al., An Interesting 5-HT3 Receptor Antagonist Antiemetic for Patients Undergoing Chemotheraphy-based Conditioning Regimens, Blood, Nov. 16, 2001, vol. 98, No. 11, part 2, p. 350b, abstract No. 5169.

Stacher, Georg, Palonosetron Helsinn, Current Opinion in Investigational Drugs. Oct. 2002, vol. 3, No. 10, pp. 1502-1507.

Navari, Rudolph M., Pathogenesis-Based Treatment of Chemotherapy-Induced Nausea and Vomiting—Two New Agents, Journal of Supportive Oncology, 2003, vol. 1(2), pp. 89-103.

Chaitow, 1990, 3 pages.

Opposition Brief filed by Dr. Reddy's Laboratories (UK) Limited, opposition to European Patent No. 1601359B1 dated Jul. 7, 2009.

Photolytic and oxidative degradation of an antiemetic agent, RG 12915 (Won C. M. et al., International Journal of Pharmaceutics 121, 95-105 (1995).

Palonosetron: a phase II dose ranging study to assess over a 7 day period the single dose pharmacokinetic profile of palonosetron in patients receiving highly emetogenic chemotherapy. Piraccini et al., Proc. Am. Soc. Clin. Oncol 2002 21 Abs 449 (2002).

Formulation and administration techniques to minimize injection pain and tissue damage associated with parenteral products. Larry A. Gatlin and Carol A. Brister Gatlin, from Injectable Drug Development: Techniques to Reduce Pain and Irritation (Edited by Pramod K. Gupta and Gayle A. Brazeau; published by Informa Health Care) 1999; ISBN 1574910957, 9781574910957, p. 401-421.

Parenteral Dosage Forms. Joanne Broadhead, from Part 11-Early drug development, pharmaceutical preformulation and formulation: a practice guide from candidate drug selection to commercial dosage form (Edited by Mark Gibson; Published by Interpharma Press, 2001; ISBN 1574911201, 9781574911206), p. 331-353.

Opposition Brief filed by Tecnimede Sociedade Tecnico-Medicinal S.A. in opposition to European Patent No. 1601359 B1, Jul. 8, 2009.

Response brief filed by Helsinn Healthcare S.A. dated Jul. 13, 2007, in response to the communication pursuant to Art. 96(2) EPC of Jan. 3, 2007 regarding Serial Number 04 706 657.6-2123.

European Patent Office official communication dated Jul. 19, 2006, regarding Serial No. 04 706 657.6.

Response of Helsinn Healthcare S.A. dated Nov. 29, 2006, regarding EPO official communication date Jul. 19, 2006.

Lachman et al., The Theory and Practice of Industrial Pharmacy, 1986, third edition, pp. 652-784.

Declaration of Valentino J. Stella, Ph.D. dated Sep. 19, 2007.

Opposition Brief filed by Martin Paul White, opposition to European Patent No. 1601359 B1, Jul. 8, 2009.

Wong et al. (1995), in British Journal of Pharmacology, vol. 114, pp. 851-859.

Cover page and pp. 642-644 and 783-784 of the Theory and Practice of Industrial Pharmacy, Third Edition, Lea and Febiger (1986).

Cover page and pp. 514-515 of Modern Pharmaceutics, Second Edition, Marcel Dekker (1990).

Cover page and pp. 142-143 of Pharmaceutical Dosage Forms: Parenteral Medications vol. 1, Second Edition, Marcel Dekker (1992).

Mitsuo Matsumoto et al., "Yakuzaigaku Manual", 1st edition, Nanzando Co., Ltd. (1989) 2 pages.

Michael J. Pikal, "Freeze Drying", Encyclopedia of Pharmaceutical Technology, Third Edition, Jan. 2007, pp. 1824-1825, vol. 3, Informa Pharmaceuticals and Healthcare.

Daniele Bonadeo, "Supplemental Declaration of Daniele Bonadeo Under 37 C.F.R. 1.132", filed in U.S. Appl. No. 11/388,270, Jun. 8, 2009.

Kranke et al., 2007 "Recent advances, trends, and economic considerations in . . . " Expert Opinion Pharmacotherp., 8(18): 3217-3235.

Morrow et al., 1995, "Progress in reducing nausea and emesis: Comparisons of ondansetron, granisetron, and tropisetron." Cancer, vol. 76, No. 3 pp. 343-357.

USPTO Notice of Allowance and Fees Due, U.S. Appl. No. 11/388,270, filed Mar. 24, 2006, Date Mailed Jan. 26, 2010.

USPTO Office Action, U.S. Appl. No. 11/129,839, Date Mailed Jan. 15, 2010.

Israili, Zafar H., "Clinical Pharmacology of Serotonin Receptor Type (5-HT3) Antagonists," Curr. Med. Chem. Central Nervous System Agents, 2001:1, 171-199.

Barton (Citrate Buffer Calculation) 2000, 2 pages.

USPTO Office Action, U.S. Appl. No. 11/201,035, Date Mailed Aug. 19, 2009.

Response of Helsinn Healthcare to opposition of EP Serial No. 04 706 657.6, dated Feb. 11, 2010.

Annex 1 (Statement of Walso Mossi, Ph.D.) to Response of Helsinn Healthcare to Opposition of EP Serial No. 04 706 657.6 dated Feb. 11, 2010.

Annex 2 to Response of Helsinn Healthcare to Opposition of EP Serial No. 04 706 657.6 dated Feb. 11, 2010.

Annex 3 to Response of Helsinn Healthcare to Opposition of EP Serial No. 04 706 657.6 dated Feb. 11, 2010.

Summary of Product Characteristics for Aloxi 250 (2009).

Scientific Discussion from the European Public Assessment Report for Aloxi (Palonoseteron Hydrochloride) 2006.

6th Edition, Handbook of Pharmaceutical Excipients (2009), pp. 247-250 (RPS Publishing).

Lewis, Gareth A (2006) 'Optimization Methods,' Encyclopedia of Pharmaceutical Technology, 1:1, 2452-2467.

May 24, 2011 Para. IV notice from Teva Pharmaceuticals re ∝724 and ∝725 patents.

May 24, 2011 Para. IV notice from Sandoz re '724 and '725 patents.

May 24, 2011 Para. IV notice from Dr. Reddy's re '724 and '725 patents.

Aug. 9, 2011 Para. IV notice from Dr. Reddy's re '424 patent.

Aug. 19, 2011 Para. IV notice from Teva Pharmaceuticals re '424 patent.

Sep. 22, 2011 Para. IV notice from Sandoz re '724, '725 and '424 patents.

Jul. 8, 2011 Complaint for patent infringement (D. N. J. case No. 11-03962).

Sep. 23, 2011 Complaint for patent infringement (D. N. J. case No. 11-5579).

Aug. 31, 2011 Answer and counterclaim of Dr. Reddy's Laboratories, Ltd. and Dr. Reddy's Laboratories, Inc. (D. N. J. case No. 11-03962).

Sep. 13, 2011 Sandoz Inc.'s answer to complaint for patent infringement and counterclaims (D. N. J. case No. 11-03962).

(56) References Cited

OTHER PUBLICATIONS

Sep. 13, 2011 Teva Pharmaceuticals USA, Inc. and Teva Pharmaceutical Industries Ltd.'s answer (D. N. J. case No. 11-03962).
Oct. 5, 2011 Plaintiffs reply to answer and counterclaim of Dr. Reddy's Laboratories, Ltd. and Dr. Reddy Laboratories, Inc. (D. N. J. case No. 11-03962).
Oct. 21, 2011 Plaintiff's reply to Sandoz Inc.'s answer to complaint for patent infringement and counterclaims (D. N. J. case No. 11-03962).
Oct. 24, 2011 Answer and counterclaim of Dr. Reddy's Laboratories, Ltd. and Dr. Reddy's Laboratories, Inc. (D. N. J. case No. 11-5579).
Oct. 24, 2011 Sandoz Inc.'s answer to complaint for patent infringement and counterclaims (D. N. J. case No. 11-5579).
Oct. 27, 2011 Order consolidating the two cases (D. N. J. case No. 11-5579).
Nov. 17, 2011 Plaintiffs' reply to answer and counterclaim of Dr. Reddy's Laboratories, Ltd. and Dr. Reddy's Laboratories, Inc. (D. N. J. case No. 11-03962).
Nov. 17, 2011 Plaintiffs' reply to Sandoz Inc.'s answer to complaint for patent infringement and counterclaims (D. N. J. case No. 11-03962).
Dec. 5, 2011 Teva Pharmaceuticals USA Inc. and Teva Pharmaceuticals Industries Ltd.'s answer to complaint for patent infringement of the '424 patent (D. N. J. case No. 11-03962).
May 21, 2012 Defendants' opening claim construction brief (including exhibits 1-31).
May 21, 2012 Plaintiffs' opening claim construction brief (including exhibits 1-15).
Jul. 20, 2012 Defendants' responsive claim construction brief (including exhibits 1-3).
Jul. 20, 2012 Plaintiffs' responsive claim construction brief (including Exhibits A and B).
Sep. 7, 2012 Court transcript from Sep. 7, 2012 Markman hearing and Plaintiffs' PowerPoint presentation (D. N. J. case No. 11-03962).
Dec. 1, 2011 Sandoz Inc.'s invalidity contentions pursuant to L. Pat. R. 3.6(c) (D. N. J. case No. 11-03962).
Dec. 1, 2011 Teva Pharmaceuticals USA, Inc. and Teva Pharmaceutical Industries, Ltd.'s invalidity contentions, pursuant to L. Pat. R. 3.6(c)(D. N. J. case No. 11-03962).
Dec. 1, 2011 Dr. Reddy's Laboratories, Ltd.'s and Dr. Reddy's Laboratories, Inc.'s invalidity contentions pursuant to L. Pat. R. 3.6(c) (D. N. J. case No. 11-03962).
Jan. 31, 2012 Plaintiff's responses to defendants' invalidity contentions (D. N. J. case No. 11-03962).
Sep. 25, 2012 Sandoz Inc.'s first amended invalidity contentions pursuant to L. Pat. R. 3.6(c) (D. N. J. case No. 11-03962).
Nov. 19, 2012 Plaintiffs' responses to Sandoz Inc.'s first amended invalidity contentions (D. N. J. case No. 11-03962).
L.G. Wade Jr., Organic Chemistry, Ch. 19: Amines, pp. 867-936 (Prentice Hall 3d ed. 1995).
L. Lachman et al., The Theory and Practice of Industrial Pharmacy, pp. 642-644, 783-784 (Lea & Febiger 3d ed. 1986).
P.P. DeLuca et al., Formulation of Small Volume Parenterals in Pharmaceutical Dosage Forms: Parenteral Medications, vol. 1, Ch. 5, pp. 173-248 (Avis, Lieberman, Lachman eds., Marcel Dekker Inc. 2d ed. 1992).
C.M. Won et al, Photolytic and Oxidative Degradation of an Antiemetic Agent, RGI2915, Int'l J Pharmaceutics 121:95-105 (1995).
R.D. Clark et al., 2-(Quinuciidin-3-yl)pyrido[4,3-b]indol-l-ones and Isoquinoin-l-ones. Potent Conformationally Restricted 5-HT3 Receptor Antagonists, J Med. Chem. 36:2645-57 (1993).
L.A. Trissel, Drug Stability and Compatibility Issues, Handbook on Injectable Drugs, pp. XI-XVI (ASHP 7th ed. 1992).
J. Broadhead, Parenteral Dosage Forms, Pharmaceutical Preformulation and Formulation: A Practical Guide from Candidate Drug Selection to Commercial Dosage Form, Ch. 9, pp. 331-54 (Gibson ed., CRC Press 1st ed. 2001).
K.A. Connors et al., Chemical Stability of Pharmaceuticals: A Handbook for Pharmacists (John Wiley & Sons 2d ed. 1986).
Zofran®, in The Physician's Desk Reference, op. 1503-07 (5th ed. 2001).
Anzemet®, in The Physician's Desk Reference, pp. 680-83 (5th ed. 2001).
Kytril®, in The Physician's Desk Reference, pp. 3104-06 (5th ed. 2001).
L.A. Trissel, Ondansetron HCI, in Handbook on Injectable Drugs, pp. 683-88 (ASHP 7th ed. 1992).
Navoban® (tropisetron HCI) Malaysian Prescribing Information (Sep. 2000).
Kytril® (granisetron HCI) South African Prescribing Information (Dec. 1993).
S. Motola and S. Agharkar, Preformulation Research of Parenteral Medications, Pharmaceutical Dosage Forms: Parenteral Medications, vol. 1, Ch. 4, pp. 115-172 (Avis, Lieberman, Lachman eds., Marcel Dekker Inc. 2d ed. 1992).
J. Wells, Pharmaceutical Preformuatlion: The Physicochemical Properties of Drug Substances, Ch. 5: Drug Stability, pp. 152-191 (Ellis Horwod Ltd. 1988).
J. Swarbrick and Boylan, Encyclopedia of Pharmaceutical Technology, Excipients Chapter: Their Role in Parenteral Dosage Forms, vol. 19(2):137-172 (Marcel Dekker, Inc. 2000).
Handbook of Pharmaceutical Excipients, 3d Ed., (Kibbe ed. Pharmaceutical Press 2000); pp. 140-143, 191-194, 324-238.
G. Stacher, Palonosetron (Helsinn), Curro. Opin. Investig. Drugs, 3(10) 1502-7 (2002).
Handbook of Modern Pharmaceutical Analysis, (S. Ahuja et al. ed., Academic Press, 2001).
Jun. 8, 2009 Bonadeo Declaration.
Jun. 8, 2009 Bonadeo Declaration, Exhibit 2.
Jun. 8, 2009 Bonadeo Declaration, Exhibit 3.
HELSN0117262-69 (2008).
HELSN0117270-312 (2012).
Feb. 13, 2007 Statutory Declaration of Daniele Bonadeo, with Exhibit A.
Nov. 21, 2007 Statutory Declaration of Giorgio Calderari, Daniele Bonadeo, Roberta Cannella, Enrico Braglia, and Riccardo Braglia.
Reddy's Paragraph IV notice regarding all three patents (D. N. J. Case No. 12-2867), dated Mar. 30, 2012.
May 11, 2012 Complaint for patent infringement filed by Helsinn and Roche (D. N. J. Case No. 12-2867).
Jun. 26, 2012 Notice of Reddy's motion to dismiss (D. N. J. Case. No. 12-2867).
Jun. 26, 2012 Dr. Reddy's Laboratories, Ltd.'s and Dr. Reddy's Laboratories, Inc.'s memorandum of law in support of their motion to dismiss or for summary judgment of non-infringement of U.S. patent No. 7,947,724 (D. N. J. Case No. 12-2867) (including Exhibits 1-10).
Aug. 16, 2012 Notice of Plaintiffs' cross-motion for partial summary judgment of infringement (D. N. J. Case No. 12-2867).
Aug. 6, 2012 Plaintiffs' opposition to Defendants' motion to dismiss or for summary judgment of noninfringement and cross-motion for partial summary judgment of infringement (D. N. J. Case No. 12-1867) (including exhibits 1-4).
Schöneich declaration (D. N. J. Case No. 12-2867) (Including Exhibits A and 1-24), dated Aug. 6, 2012.
Sep. 4, 2012 Reddy's brief in opposition to Plaintiffs' cross-motion for partial summary judgment and reply memorandum of law in further support of Reddy's motion to dismiss or for summary judgment of non-infringement (D. N. J. Case No. 12-2867)(Including Exhibits 1-4).
DeLuca Declaration (D. N. J. Case No. 12-2867)(Including exhibits A-J), dated Sep. 3, 2012.
Sep. 10, 2012 Plaintiffs' letter to Judge Cooper in response to Reddy's combined opposition to Plaintiffs' cross-motion for partial summary judgment and reply in support of Reddy's motion to dismiss or for summary judgment of noninfringement (D. N. J. Case No. 12-2867)(including exhibits A and B).
Sep. 14, 2012 Dr. Reddy's letter in response to Plaintiffs' Sep. 10, 2012 letter (D. N. J. Case No. 12-2867).
USPTO Office Action, U.S. Appl. No. 11/388,268, filed Mar. 24, 2006, Mail Date Mar. 29, 2010.
USPTO Non-Final Office Action, U.S. Appl. No. 11/186,311, mailed Aug. 30, 2006.

(56) References Cited

OTHER PUBLICATIONS

USPTO Non-Final Office Action, U.S. Appl. No. 11/186,311, mailed Oct. 5, 2007.
USPTO Non-Final Office Action, U.S. Appl. No. 11/186,311, mailed Oct. 6, 2008.
USPTO Final Office Action, U.S. Appl. No. 11/186,311, mailed May 20, 2009.
USPTO Advisory Action, U.S. Appl. No. 11/186,311, mailed Jul. 15, 2009.
USPTO Notice of Allowance and Fees Due, U.S. Appl. No. 11/186,311, mailed Mar. 4, 2011.
USPTO Notice of Allowability, U.S. Appl. No. 11/186,311, dated May 24, 2011.
USPTO Non-Final Office Action, U.S. Appl. No. 11/388,268, mailed Jul. 17, 2006.
USPTO Non-Final Office Action, U.S. Appl. No. 11/388,268, mailed Nov. 17, 2006.
USPTO Non-Final Office Action, U.S. Appl. No. 11/388,268, mailed Oct. 3, 2007.
USPTO Non-Final Office Action, U.S. Appl. No. 11/388,268, mailed Mar. 26, 2008.
USPTO Final Office Action, U.S. Appl. No. 11/388,268, mailed Nov. 12, 2008.
USPTO Non-Final Office Action, U.S. Appl. No. 11/388,268, mailed Jul. 15, 2009.
USPTO Notice of Allowance and Fees Due, U.S. Appl. No. 11/388,268, mailed Dec. 22, 2010.
USPTO Non-Final Office Action, U.S. Appl. No. 11/388,269, mailed Jul. 19, 2006.
USPTO Non-Final Office Action, U.S. Appl. No. 11/388,269, mailed Nov. 17, 2006.
USPTO Non-Final Office Action, U.S. Appl. No. 11/388,269, mailed Sep. 20, 2007.
USPTO Non-Final Office Action, U.S. Appl. No. 11/388,269, mailed Jul. 9, 2008.
USPTO Interview Summary, U.S. Appl. No. 11/388,269, dated Apr. 28, 2009.
USPTO Final Office Action, U.S. Appl. No. 11/388,269, mailed May 20, 2009.
USPTO Advisory Action, U.S. Appl. No. 11/388,269, mailed Jul. 15, 2009.
USPTO Notice of Abandonment, U.S. Appl. No. 11/388,269, mailed Dec. 18, 2009.
USPTO Non-Final Office Action, U.S. Appl. No. 11/388,270, mailed Jul. 13, 2006.
USPTO Interview Summary, U.S. Appl. No. 11/388,270, dated Aug. 3, 2006.
USPTO Non-Final Office Action, U.S. Appl. No. 11/388,270, mailed Nov. 16, 2006.
USPTO Non-Final Office Action, U.S. Appl. No. 11/388,270, mailed Sep. 20, 2007.
USPTO Interview Summary, U.S. Appl. No. 11/388,270, dated Dec. 14, 2007.
USPTO Non-Final Office Action, U.S. Appl. No. 11/388,270, mailed Mar. 25, 2008.
USPTO Final Office Action, U.S. Appl. No. 11/388,270, mailed Oct. 29, 2008.
USPTO Advisory Action, U.S. Appl. No. 11/388,270, mailed Jan. 23, 2009.
USPTO Non-Final Office Action, U.S. Appl. No. 11/388,270, mailed Jul. 9, 2009.
USPTO Interview Summary, U.S. Appl. No. 11/388,270, dated Nov. 12, 2010.
USPTO Notice of Allowance and Fees Due, U.S. Appl. No. 11/388,270, mailed Jan. 5, 2011.
USPTO Non-Final Office Action, U.S. Appl. No. 13/087,012, mailed Mar. 12, 2012.
USPTO Non-Final Office Action, U.S. Appl. No. 13/087,012, mailed Jul. 19, 2012.
USPTO Interview Summary, U.S. Appl. No. 13/087,012, dated Feb. 15, 2013.
USPTO Notice of Allowance and Fees Due, U.S. Appl. No. 13/087,012, mailed Feb. 27, 2013.
USPTO Response to Amendment under Rule 312, U.S. Appl. No. 13/087,012, mailed Apr. 4, 2013.
USPTO Notice of Allowance and Fees Due, U.S. Appl. No. 13/087,012, mailed Jul. 3, 2013.
USPTO Non-Final Office Action and Examiner-Initiated Interview Summary, U.S. Appl. No. 13/901,437, mailed Jul. 29, 2013.
USPTO Non-Final Office Action, U.S. Appl. No. 13/902,132, mailed Aug. 8, 2013.
USPTO Interview Summary, U.S. Appl. No. 13/087,012 dated Jun. 13, 2013.
USPTO Notice of Allowance and Fees Due and Examiner-Initiated Interview Summary, U.S. Appl. No. 13/901,288, mailed Sep. 6, 2013.
Feb. 9, 2009 Bonadeo Declaration.
CDER Approval Package for NDA 21-372, Clinical Pharmacology and Biopharmaceutics Review (2002).
USPTO Non-Final Office Action, U.S. Appl. No. 11/129,839, mailed Jun. 10, 2008.
Eisenberg et al. 2004, "Efficacy, safety and pharmacokinetics of palonosetron in patients receiving highly emetogenic cisplatin-based chemotherapy: a dose-ranging clinical study. "Annals of Oncology, vol. 15, pp. 330-337.
Mayron et al. 1996, "Stability and compatibility of granistron hydrochloride in i.v. solutions and oral liquids and during simulated Y-site injection with selected drugs." Am J Health-Sys Pharm, 53: 294-304.
Trissel et al. 1997, "Compatibility of granisetron hydrochloride with selected drugs during simulated Y -site administration." Am J Health-Syst Pharm 54: 56-60.
USPTO Final Office Action, U.S. Appl. No. 11/129,839, mailed Mar. 17, 2009.
USPTO Advisory Action, U.S. Appl. No. 11/129,839, mailed Jul. 22, 2009.
USPTO Non-Final Office Action, U.S. Appl. No. 11/129,839, mailed Jan. 15, 2010.
USPTO Examiner Interview Summary, U.S. Appl. No. 11/129,839, mailed Nov. 9, 2010.
USPTO Notice of Allowance and Fees Due, U.S. Appl. No. 11/129,839, mailed Jan. 3, 2011.
USPTO Notice of Abandonment, U.S. Appl. No. 11/129,839, mailed Apr. 18, 2011.
USPTO Non-Final Office Action, U.S. Appl. No. 13/077,374, mailed Feb. 17, 2012.
Roila et al. 1998, "Prevention of chemotherapy- and radiotherapy-induced emesis: Results of the Perugia consensus conference." Annals of Oncology, vol. 9, pp. 811-819.
USPTO Final Office Action, U.S. Appl. No. 13/077,374, mailed Nov. 23, 2012.
Piraccini, Gaia et al., American Society of Clinical Oncology May 12-15, 2001 San Francisco—USA (vol. 20, part 1 of 2, 2001) (Abstract No. 1595).
USPTO Non-Final Office Action, U.S. Appl. No. 11/201,035, mailed May 16, 2008.
USPTO Final Office Action, U.S. Appl. No. 11/201,035, mailed Feb. 4, 2009.
USPTO Final Office Action, U.S. Appl. No. 11/201,035, mailed Jun. 8, 2010.
USPTO Non-Final Office Action, U.S. Appl. No. 13/901,830, mailed Nov. 22, 2013.
USPTO Non-Final Office Action and Applicant-Initiated Interview Summary, U.S. Appl. No. 13/900,174, mailed Nov. 19, 2013.
USPTO Non-Final Office Action, U.S. Appl. No. 14/184,305, mailed May 29, 2014.
USPTO Applicant-Initiated Interview Summary, U.S. Appl. No. 14/184,305, dated Jul. 18, 2014.
USPTO Non-Final Office Action, U.S. Appl. No. 13/902,299, mailed Dec. 5, 2013.
USPTO Final Office Action, U.S. Appl. No. 13/902,132, mailed Dec. 6, 2013.
USPTO Non-Final Office Action, U.S. Appl. No. 14/052,925, dated Dec. 4, 2013.

(56) References Cited

OTHER PUBLICATIONS

USPTO Non-Final Office Action, U.S. Appl. No. 14/070,981, mailed Nov. 4, 2014.
FDA approval letter of Aloxi (palonosetron hydrochloride injection), dated Jul. 25, 2003.
Macciocchi A, Chernoff SB, Gallagher SC. A phase II dose-ranging study to assess intravenous doses of palonosetron for the prevention of highly emetogenic chemotherapy-induced nausea and vomiting. In: Program/Proceedings of the 38th Annual Meeting of the American Society of Clinical Oncology; May 18-21, 2002; Orlando, Fla. Abstract 1480.
Grunberg SM, Hajdenberg J, Charu V, et al. Palonosetron is active in preventing acute and delayed emesis following moderately emetogenic chemotherapy: results of a phase III trial. Support Care Cancer 2002;10:Abstract P-113.
Aapro MS, Selak E, Lichinitser M, et al. Palonosetron is more effective than ondansetron in preventing chemotherapy-induced nausea and vomiting in patients receiving moderately emetogenic chemotherapy: results of a phase III trial. In: Program/Proceedings of the 39th Annual Meeting of the American Society of Clinical Oncology; May 31-Jun. 3, 2003; Chicago, Ill. Abstract 2918.
Aapro MS, Bertoli L, Lordick F, et al. Palonosetron is effective in preventing acute and delayed chemotherapy induced nausea and vomiting in patients receiving highly emetogenic chemotherapy. $15^{th}$ MASCC International Symposium, Berlin, Germany. Support Care Cancer, vol. 11, No. 6, Jun. 2003, A17.
Cartmell AD, Ferguson S, Yanagihara R, et al. Protection against chemotherapy-induced nausea and vomiting is maintained over multiple cycles of moderately or highly emetogenic chemotherapy by palonosetron, a potent 5 HT3 receptor antagonist. In: Program/Proceedings of the 39th Annual Meeting of the American Society of Clinical Oncology; May 31-Jun. 3, 2003; Chicago, Ill. Abstract 3041.
Sabra, Choice of a 5-HT3 Receptor Antagonist for the Hospital Formulary, EHP, Oct. 1996, vol. 2, Supp 1, S19-S24.
Gregory and Ettinger, 5HT3 receptor antagonists for the prevention of chemotherapy-induced nausea and vomitting. A comparison of their pharmacology and clinical efficacy. Drugs, Feb. 1998; 55(2): 173-189.
Full Prescribing Information for Aloxi (palonosetron HCl) injection for Intravenous Use (2008).
Drug, Dose & Schedule Recommendations for Antiemetic Regimens (American Society for Clinical Oncology) (2006).
Yamakuni, et al., The Journal of Pharmacology and Experimental Therapeutics, Probable Involvement of the 5-Hydroxytryptamine4 Receptor in Methotrexate-Induced Delayed Emesis in Dogs, 2000, The American Society for Pharmacology and Experimental Therapeutics, vol. 292, No. 3, p. 1002-1294.
Geling, et al., Should 5-Hydroxytryptamine-3 Receptor Antagonists Be Administered Beyond 24 Hours After Chemotherapy to Prevent Delayed Emesis? Systematic Re-Evaluation of Clinical Evidence and Drug Cost Implications, Journal of Clinical Oncology, vol. 23, No. 6, Feb. 20, 2005 (American Society of Clinical Oncology), pp. 1289-1294.
Rojas, et al., International Anesthesia Research Society, Palonosetron Exhibits Unique Molecular Interactions with 5-HT3 Receptor, vol. 107, No. 2, Aug. 2008, p. 469-478.
Rojas, et al., Palonosetron triggers 5-HT3 receptor internalization and causes inhibition of receptor function, European Journal of Pharmacology 626 (2010), p. 193-199.
Regan-Shaw, et al., Dose translation from animal to human studies revisited, The FASEB Journal, Life Sciences Forum (2008), p. 659-661.
Saito, et al., Palonosetron plus dexamethasone versus granisetron plus dexamethasone for prevention of anusea and vomiting during chemotherapy: a double-blind, double-dummy, randomised, comparative phased III trial, www.thelancet.com/oncology, vol. 10, Feb. 2009, p. 115-124.
Palonosetron: more than just another option?. www.thelancet.com/oncology, vol. 10, Feb. 2009, p. 100-101.
Lorusso, et al., Single dose of palonosetron plus dexamethasone to control nausea, vomiting and to warrant an adequate food intake in patients treated with highly emetogenic chemotherapy (HEC). Preliminary results, Support Care Cancer, published online Mar. 18, 2009.
Grunberg, et al., Effectiveness of a single-day three-drug regimen of dexamethasone, palonosetron, and aprepitant for the prevention of acute and delayed nausea and vomiting caused by moderately emetogenic chemotherapy, Support Care Cancer (2009) 17:589-594.
Celio, et al., Clinical update on palonosetron in the management of chemotherapy-induced nausea and vomiting, Tumor, 94: 447-452, 2008.
Ellebaek, et al., Optimizing antiemetic therapy in multiple-day and multiple cycles of chemotherapy, Lippincott williams & Wilkins, Current Opinion in Supportive and Palliative Care, 2008, 2:28-34.
Herrington, et al., Randomized, Placebo-controlled, Pilot Study Evaluating Aprepitant Single Dose Plus Palonosetron and Dexamethasone for the Prevention of Acute and Delayed Chemotherapy-induced Nausea and Vomiting, American Cancer Society, published online Mar. 7, 2008 in Wiley InterScience (www.interscience.wiley.com).
Massa, et al., Palonosetron plus dexamethasone effectively prevents acute and delayed chemotherapy-induced nausea and vomiting following highly or moderately emetogenic chemotherapy in pretreated patients who have failed to respond to a previous antiemetic treatment: Comparison between elderly and non-elderly patient response, Critical Reviews in Oncology/Hematology 70 (2009) 83-91.
2006 Update of the ASCO Recommendations for Antiemetics in Oncology: Guideline Summary, American Cancer Society of Clinical Oncology, Jul. 2006, www.jopasco.org.
Warr, David, Standard treatment of chemotherapy-induced emesis, Support Care Cancer, vol. 5, pp. 12-16, 1997.
Aapro, M.S., et al. A phase III, double-blind, randomized trial of palonosetron compared with ondansetron in preventing chemotherapy-induced nausea and vomiting following highly emetogenic chemotherapy. Annals of Oncology, vol. 17, pp. 1441-1449, 2006.
Eisenberg, Peter, et al. Improved Prevention of Moderately Emetogenic Chemotherapy-Induced Nausea and Vomiting with Palonosetron, a Pharmacologically Novel 5-HT3 Receptor Antagonist. Cancer, vol. 98, No. 11, pp. 2473-2482, Dec. 1, 2003.
Gandara, D.R., et al. The delayed-emesis syndrome from cisplatin: Phase III evaluation of ondansetron versus placebo. Semin Oneal vol. 19, No. 4, pp. 67-71, Aug. 1992 (suppl 10).
Goedhals, L., et al. Control of delayed nausea and vomiting with granisetron plus dexamethasone or dexamethasone alone in patients receiving highly emetogenic chemotherapy: A double-blind, placebo-controlled, comparative study. Ann Oneal, vol. 9, pp. 661-666, 1998.
Gralla, R., et al. Palonosetron improves prevention of chemotherapy-induced nausea and vomiting following moderately emetogenic chemotherapy: results of a double-blind randomized phase III trial comparing single doses of palonosetron with ondansetron. Annals of Oncology, vol. 14, pp. 1570-1577, 2003.
Italian Group for Antiemetic Research. Dexamethasone alone or in combination with ondansetron for the prevention of delayed nausea and vomiting induced by chemotherapy. N. Engl J Med, vol. 342, No. 21, pp. 1554-1559, May 25, 2000.
Kaizer, L., et al. Effect of schedule and maintenance on the antiemetic efficacy of ondansetron combined with dexamethasone in acute and delayed nausea and emesis in patients receiving moderately emetogenic chemotherapy: A phase III trial by the National Cancer Institute of Canada Clinical Trials Group. J Clin Oncol, vol. 12, No. 5, pp. 1050-1057, May 1994.
Latreille, J., et al. Use of dexamethasone and granisetron in the control of delayed emesis for patients who receive highly emetogenic chemotherapy: National Cancer Institute of Canada Clinical Trials Group. J Clin Oncol, vol. 16, No. 3, pp. 1174-1178, Mar. 1998.
Antiemetic Subcommittee of the Multinational Association of Supportive Care in Cancer (MCSCC). Prevention of chemotherapy—and—radiotherapy-induced emesis: Results of the Perugia Consensus Conference. Annals of Oncology, vol. 9, pp. 811-819, 1998.

(56) References Cited

OTHER PUBLICATIONS

Moyer, Paula. New Understanding of Emesis Pathways Leading to New Treatment, Better Control. Oncology Times, vol. 25, Issue 10, pp. 48-51, May 25, 2003.
Navari, R.M., et al. Oral ondansetron for the control of cisplatin-induced delayed emesis: A large, multicenter, double-blind, randomized comparative trial of ondansetron versus placebo. J Clin Oncol, vol. 13, No. 9, pp. 2408-2416, Sep. 1995.
Olver, I., et al. A multicenter, double-blind study comparing placebo, ondansetron and ondansetron plus dexamethasone for the control of cisplatin-induced delayed emesis. Ann Oncol, vol. 7, pp. 945-952, 1996.
Pater, J.L., et al. The role of the 5-HT3 antagonists ondansetron and dolasetron in the control of delayed onset nausea and vomiting in patients receiving moderately emetogenic chemotherapy. Ann Oncol, vol. 8, pp. 181-185, 1997.
Rojas, Camilo, et al. The Antiemetic 5-HT3 Receptor Antagonist Palonosetron Inhibits Substance P—Mediated Responses in Vitro and in Vivo. J Pharmacal Exper Thera, vol. 335, No. 2, pp. 362-368, 2010.
Sorbe, B. G., et al. A study evaluating the efficacy and tolerability of tropisetron in combination with dexamethasone in the prevention of delayed platinum-induced nausea and emesis. Cancer, vol. 83, pp. 1022-1032, 1998.
Stewart, A., et al. Ondansetron Compared with Granisetron in the Prophylaxis of Cyclophosphamide-Induced Emesis in Out-Patients: A Multicentre, Double-Blind, Double-Dummy, Randomised, Parallel-Group Study. Oncology, vol. 52, pp. 202-210, 1995.
Weiderpass, Elisabete, et al. Use of an NK1 Receptor Antagonist to Prevent Delayed Emesis After Cisplatin. Journal of the National Cancer Institute, vol. 89, No. 11, pp. 817-818, Jun. 4, 1997.
Akers, Michael J., Excipient-Drug Interactions in Parenteral Formulations. Journal of Pharmaceutical Sciences, vol. 91, No. 11, Nov. 2002, pp. 2283-2300.
Maemondo, et al., A phase II study of palonosetron combined with dexamethasone to prevent nausea and vomiting induced by highly emetogenic chemotherapy. Annals of Oncology, Nov. 2009, vol. 20, No. II, pp. 1860-1866.
Program/Proceedings American Society of Clinical Oncology, vol. 20, Part 1 of 2, 2001, Abstract No. 1595 and associated poster presentation.
Saito, et al., Review of palonosetron: emerging data distinguishing it as a novel 5-HT3 receptor antagonist for chemotherapy-induced nausea and vomiting. Expert Opin. Pharmacother (2010) II (6), pp. 1003-1014.
Perez, et al., Comparable safety and antiemetic efficacy of a brief (30-second bolus) intravenous granisetron infusion and a standard (15-minute) intravenous ondansetron infusion in breast cancer patients receiving moderately emetogenic chemotherapy. Cancer J. Sci. Am. vol. 4, No. 1, pp. 52-58, 1998.
MGI-HHC__SEC__filing (2001).
ROCHE0008749-876 (1995) (portions redacted).
HELSN0135068-82 (1998).
English-language translation of Italian-language portions of HELSN0135068-82 (1998).
HELSN0161327-348 (2000) (portions redacted).
HELSN0138407-24 (1998) (portions redacted).
HELSN0376401-469 (2002) (portions redacted).
HELSN0392650-72 (1999) (portions redacted).
Dr. Reddy's Labs., Ltd.'s and Dr. Reddy's Labs., Inc.'s Memorandum of Law in Support of Their Motion to Amend Their Invalidity Contentions dated Feb. 15, 2013 (D.N. J. Case No. 11-3962).
HELSN0376719-21 (2001).
HELSN0376722-23 (2001).
HELSN0376724 (2002).
Dr. Reddy's Laboratories, Ltd.'s and Dr. Reddy's Laboratories, Inc.'s Redline of Proposed Amended Invalidity Contentions Pursuant to L. Pat. R. 3.6(c) filed Feb. 15, 2013 (D.N. J. Case No. 11-3962).
Dr. Reddy's Laboratories, Ltd.'s and Dr. Reddy's Laboratories, Inc.'s Reply Memorandum of Law in Further Support of Their Motion to Amend Their Invalidity Contentions dated Mar. 15, 2013 (D.N. J. Case No. 11-3962).
Teva Pharm. Indus., Ltd.'s and Teva Pharm. USA, Inc.'s Memorandum in Support of Their Motion to Amend Invalidity Contentions dated Feb. 15, 2013 (D.N. J. Case No. 1-3962).
HELSN0388553-65 (1998).
HELSN0388566-68 (1998).
HELSN0388569-74 (1998).
HELSN0388587-91 (1998).
HELSN0388592-95 (1998).
English-language translation of HELSN0388592-95 (1998).
HELSN0388596-97 (1998).
HELSN0388604 (1998).
HELSN0388605-06 (1998).
HELSN0388607-09 (1998).
HELSN0389134-44 (1999).
HELSN0389145-48 (1999).
HELSN0389149-61 (2000).
HELSN0392047-48 (1998).
HELSN0392393-94 (1998).
HELS0393657-61 (2000).
English-language translation of Italian-language portions of HELSN039657-61 (2000).
Excerpts from Calderari Deposition Transcript, pp. 1-4, 229-232, and 278-393 (2013).
HELSN0000093-9 (2006).
HELSN0004207 (2002).
HELSN0004217 (2002).
Teva Pharm. Indus., Ltd.'s and Teva Pharm. USA, Inc.'s Reply in Support of Their Motion to Amend Their Invalidity Contentions dated Mar. 15, 2013 (D.N. J. Case No. 1-3962).
HELSN00388448-542 (1998-1999).
English-language translation of Italian-language portions of HELSN00388448-542 (1998-1999) (portions redacted).
HELSN0388543-44 (1999).
HELSN0388545-52 (1998).
HELSN0388575-76 (1998).
HELSN0388577-80 (1998).
HELSN0388581-82 (1998).
HELSN0388583-84 (1998).
HELSN0388585 (1998).
HELSN0388586 (1998).
HELSN0388598-601 (1998).
HELSN0388602-03 (1998).
HELSN0388610 (1998).
Sandoz Inc.'s Redacted Memorandum of Law in Support of its Motion to Amend its Invalidity Contentions dated Feb. 15, 2013 (D.N. J. Case No. 11-3962).
Exhibit G to Sandoz Inc.'s Redacted Memorandum of Law in Support of its Motion to Amend its Invalidity Contentions dated Feb. 15, 2013 (D.N. J. Case No. 11-3962).
Sandoz Inc.'s Redacted Reply Memorandum of Law in Support of its Motion to Amend its Invalidity Contentions dated Mar. 15, 2013 (D.N. J. Case No. 11-3962).
Aurobindo Pharma Ltd. Paragraph IV notice regarding U.S. Patent Nos. 7,947,724; 7,947,725; and 7,960,424, dated Mar. 5, 2013 (D. Del. Case No. 13-688).
Complaint for patent infringement filed by Helsinn Healthcare S.A. and Roche Palo Alto LLC against Aurobindo Pharma Ltd. and Aurobindo Pharma USA Inc. dated Apr. 16, 2013 (D. Del. Case No. 13-688).
Accord Healthcare, Inc. Paragraph IV notice regarding U.S. Patent Nos. 7,947,724; 7,947,725; and 7,960,424, dated Apr. 3, 2013.
Bedford Laboratories division of Ben Venue Laboratories, Inc. Paragraph IV Letter regarding U.S. Patent Nos. 7,947,724, 7,947,725, and 7,960,424, dated Aug. 13, 2013.
Defendants Aurobindo Pharma Ltd.'s and Aurobindo Pharma USA Inc.'s Answer, Affirmative Defenses, and Counterclaims, dated Aug. 23, 2013 (D. Del. Case No. 13-688).

(56) References Cited

OTHER PUBLICATIONS

Plaintiffs Answer to the Counterclaims of Aurobindo Pharma USA Inc. and Aurobindo Pharma Ltd., dated Sep. 13, 2013 (D. Del. Case No. 13-688).
Aurobindo Pharma Ltd. Paragraph IV notice regarding U.S. Patent No. 8,518,981, dated Sep. 19, 2013 (portions redacted).
Dr. Reddy's Laboratories, Ltd.'s and Dr. Reddy's Laboratories, Inc.'s Amended Invalidity Contentions Pursuant to L. Pat. R. 3.6(c), dated Jul. 8, 2013 (D.N. J. Case Nos. 11-3962 and 11-5579; consolidated).
Plaintiffs' Responses to Dr. Reddy's Laboratories, Ltd. and Dr. Reddy's Laboratories, Inc.'s Amended Invalidity Contentions, dated Aug. 19, 2013 (D. N. J. Case Nos. 11-3962 and 11-5579; consolidated) (confidentiality designation redacted).
Sandoz Inc.'s Second Amended Invalidity Contentions Pursuant to L. Pat. R. 3.7, dated Jul. 5, 2013 (D.N. J. Case Nos. 11-3962 and 11-5579; consolidated) (confidentiality designation and other portions redacted).
Plaintiffs' Responses to Sandoz Inc.'s Second Amended Invalidity Contentions, dated Aug. 19, 2013 (D. N. J. Case Nos. 11-3962 and 11-5579; consolidated) (confidentiality designation and other portions redacted).
Defendants Teva Pharmaceuticals USA, Inc. and Teva Pharmaceutical Industries, Ltd.'s First Amended Invalidity Contentions Pursuant to L. Pat. R. 3.6(c), dated Jul. 5, 2013 (D.N. J. Case Nos. 11-3962 and 11-5579; consolidated) (confidentiality designation redacted).
Plaintiffs' Responses to Teva Pharmaceuticals USA, Inc. and Teva Pharmaceutical Industries, Ltd.'s First Amended Invalidity Contentions, dated Aug. 19, 2013 (D. N. J. Case Nos. 11-3962 and 11-5579; consolidated) (confidentiality designation redacted).
Opening Expert Report of Dr. Bert Spilker, dated Sep. 9, 2013 (D.N. J. Case Nos. 11-3962 and 11-5579; consolidated) (confidentiality designation and other portions redacted).
Expert Report of David G. Frame, Pharm.D., dated Sep. 5, 2013 (D.N. J. Case Nos. 11-3962 and 11-5579; consolidated) (confidentiality designation and other portions redacted).
Expert Report of Lee Kirsch, Ph.D., dated Sep. 9, 2013 (D.N. J. Case Nos. 11-3962 and 11-5579; consolidated) (confidentiality designation and other portions redacted).
Expert Report of Patrick P. DeLuca, Ph.D., dated Sep. 9, 2013 (D.N. J. Case Nos. 11-3962 and 11-5579; consolidated) (confidentiality designation and other portions redacted).
Expert Report of Paul Myrdal, Ph.D., dated Sep. 9, 2013 (D.N. J. Case Nos. 11-3962 and 11-5579; consolidated) (confidentiality designation and other portions redacted).
Complaint for patent infringement filed by Helsinn Healthcare SA and Roche Palo Alto LLC against Ben Venue Laboratories, Inc. d/b/a Bedford Laboratories regarding U.S. Patent Nos. 7,947,724, 7,947,725, 7,960,424, and 8,518,981 dated Sep. 25, 2013 (D. Del. Case No. 13-1612).
Complaint for patent infringement filed by Helsinn Healthcare SA and Roche Palo Alto LLC against Dr. Reddy's Laboratories, Ltd., Dr. Reddy's Laboratories, Inc., Sandoz Inc., Teva Pharmaceuticals USA, Inc., and Teva Pharmaceutical Industries, Ltd. regarding U.S. Patent No. 8,518,981 dated Sep. 30, 2013 (D.N. J. Case No. (13-5815)).
Reply Expert Report of Patrick P. DeLuca, Ph.D., dated Nov. 22, 2013 (D.N. J. Case Nos. 11-3962 and 11-5579; consolidated) (confidentiality designation redacted).
Reply Expert Report of David G. Frame, Pharm. D., dated Nov. 27, 2013 (D.N. J. Case Nos. 11-3962 and 11-5579; consolidated) (confidentiality designation redacted).
Reply Expert Report of Jack Geltosky, Ph.D., dated Nov. 22, 2013 (D.N. J. Case Nos. 11-3962 and 11-5579; consolidated) (confidentiality designation and other portions redacted).
Reply Expert Report of Lee Kirsch, Ph.D., dated Nov. 22, 2013 (D.N. J. Case No. 11-3962 and 11-5579; consolidated) (confidentiality designation redacted).
Reply Expert Report of Paul Myrdal, Ph.D., dated Nov. 22, 2013 (D.N. J. Case No. 11-3962 and 11-5579; consolidated) (confidentiality designation redacted).
Reply Expert Report of Dr. Bert Spilker, dated Nov. 22, 2013 (D.N. J. Case No. 11-3962 and 11-5579; consolidated) (confidentiality designation and other portions redacted).
Accord Healthcare, Inc. Paragraph IV Letter regarding U.S. Patent No. 8,518,981 dated Oct. 2, 2013 (portions redacted).
Bedford Laboratories division of Ben Venue Laboratories, Inc. Paragraph IV Letter regarding U.S. Patent No. 8,518,981 dated Oct. 16, 2013 (portions redacted).
Sandoz Inc. Paragraph IV Letter regarding U.S. Patent No. 8,518,981 dated Dec. 16, 2013.
Aurobindo Pharma Ltd. Paragraph IV Letter regarding U.S. Patent Nos. 8,598,218 and 8,598,219 dated Jan. 21, 2014 (portions redacted).
Sandoz Inc. Paragraph IV Letter regarding U.S. Patent Nos. 8,598,218 and 8,598,219 dated Feb. 3, 2014 (portions redacted).
Bedford Laboratories division of Ben Venue Laboratories, Inc. Paragraph IV Letter regarding U.S. Patent Nos. 8,598,218 and 8,598,219 dated Feb. 6, 2014 (portions redacted).
Defendants Aurobindo Pharma Ltd.'s and Auromedics Pharma LLC's Amended Answer, Affirmative Defenses, and Counterclaims regarding U.S. Patent Nos. 7,947,724, 7,947,725, 7,960,424, 8,518,981, 8,598,218, and 8,598,219, dated Feb. 11, 2014 (D. Del. Case No. 13-688).
Ben Venue Laboratories, Inc.'s Answer and Counterclaims to Amended Complaint regarding U.S. Patent Nos. 7,947,724, 7,947,725, 7,960,424, 8,518,981, 8,598,218, and 8,598,219, dated Feb. 24, 2014 (D. Del. Case No. 13-1612).
Answer and Counterclaim of Dr. Reddy's Laboratories, Ltd. and Dr. Reddy's Laboratories, Inc. to Amended Complaint for Patent Infringement regarding U.S. Patent Nos. 8,518,981, 8,598,218, and 8,598,219, dated Feb. 3, 2014 (D.N. J. Case No. 13-5815).
Sandoz Inc.'s Answer, Affirmative Defenses, and Counterclaims to Amended Complaint regarding U.S. Patent Nos. 8,518,981, 8,598,218, and 8,598,219, dated Feb. 3, 2014 (D.N. J. Case No. 13-5815).
Defendants Teva Pharmaceuticals USA, Inc. and Teva Pharmaceutical Industries Ltd.'s Answer to Amended Complaint for Patent Infringement regarding U.S. Patent Nos. 8,518,981, 8,598,218, and 8,598,219, dated Feb. 3, 2014 (D.N. J. Case No. 13-5815).
Complaint for Patent Infringement filed by Helsinn Healthcare S.A. and Roche Palo Alto LLC against Accord Healthcare, Inc. and Intas Pharmaceuticals Ltd regarding U.S. Patent Nos. 8,598,218 and 8,598,219 dated Dec. 27, 2013 (D. Del. Case No. 13-2101).
Cipla Limited Paragraph IV Letter regarding U.S. Patent Nos. 7,947,724, 7,947,725, 7,960,424, 8,518,981, 8,598,218, and 8,598,219 dated Feb. 24, 2014 (portions redacted).
Dr. Reddy's Laboratories, Ltd.'s and Dr. Reddy's Laboratories, Inc.'s Invalidity Contentions regarding U.S. Patent Nos. 8,518,981, 8,598,218, and 8,598,219 dated Mar. 17, 2014 (D.N. J. Case No. 13-5815) (confidentiality designation and other portions redacted).
Sandoz Inc.'s Invalidity Contentions Pursuant to L. Pat. R. 3.3 and 3.6(c) regarding U.S. Patent Nos. 8,518,981, 8,598,218, and 8,598,219 dated Mar. 17, 2014 (D.N. J. Case No. 13-5815) (confidentiality designation and other portions redacted).
Teva Pharmaceuticals USA, Inc. and Teva Pharmaceutical Industries Ltd.'s Invalidity Contentions Pursuant to L. Pat. R. 3.6(c) regarding U.S. Patent Nos. 8,518,981, 8,598,218, and 8,598,219 dated Mar. 17, 2014 (D.N. J. Case No. 13-5815) (confidentiality designation and other portions redacted).
Teva Pharmaceuticals USA, Inc Paragraph IV Letter regarding U.S. Patent Nos. 8,518,981, 8,598,218, and 8,598,219, dated Apr. 29, 2014 (portions redacted).
Mylan Institutional LLC Paragraph IV Letter regarding U.S. Patent Nos. 7,947,724, 7,947,725, 7,960,424, 8,518,981, 8,598,218, and 8,598,219, dated May 16, 2014 (portions redacted).
Bedford Laboratories division of Ben Venue Laboratories, Inc. Paragraph IV Letter regarding U.S. Patent No. 8,729,094, dated May 29, 2014 (portions redacted).
Defendants' Opening Claim Construction Brief regarding U.S. Patent No. 8,598,219, dated Jun. 19, 2014 (D.N. J. 11-3962, consolidated).
Answer, Affirmative Defenses and Counterclaims of Defendants Cipla Ltd. and Cipla USA, Inc. regarding U.S. Patent Nos. 7,947,724,

(56) References Cited

OTHER PUBLICATIONS 7,947,725, 7,960,424, 8,518,981, 8,598,218 and 8,598,219 dated Apr. 29, 2014 (D. Del. Case No. 14-427).
Complaint for Patent Infringement filed by Helsinn Healthcare S.A. and Roche Palo Alto LLC against Mylan Inc. and Mylan Institutional LLC regarding U.S. Patent Nos. 7,947,724, 7,947,725, 7,960,424, 8,598,219, and 8,729,094, dated Jun. 4, 2014 (D. Del. Case No. 14-709).
G. Steele, Preformulation predictions from small amounts of compound as an aid to candidate drug selection, in Pharmaceutical Preformulation and Formulation: A Practical Guide from Candidate Drug Selection to Commercial Dosage Form, Ch. 3, pp. 21-95 (Gibson ed., CRC Press 1st ed. 2001).
G. Steele, Preformulation as an aid to product design in early drug development, in Pharmaceutical Preformulation and Formulation: A Practical Guide from Candidate Drug Selection to Commercial Dosage Form, Ch. 6, pp. 175-237 (Gibson ed., CRC Press 1st ed. 2001).
M. Gibson, Product optimisation, in Pharmaceutical Preformulation and Formulation: A Practical Guide from Candidate Drug Selection to Commercial Dosage Form, Ch. 8, pp. 295-329 (Gibson ed., CRC Press 1st ed. 2001).
Mylan Institutional LLC Paragraph IV Letter regarding U.S. Patent No. 8,729,094, dated Jun. 27, 2014 (portions redacted).
Ben Venue Laboratories, Inc.'s Opening Claim Construction Brief, dated Apr. 17, 2014 (D. Del. Case No. 13-688, consolidated).
Ben Venue Laboratories, Inc.'s Answering Claim Construction Brief, dated Jul. 8, 2014 (D. Del. Case No. 13-688, consolidated).
Answer, Defenses and Counterclaims of Mylan Institutional LLC regarding U.S. Patent Nos. 7,947,724, 7,947,725, 7,960,424, 8,598,219, and 8,729,094, dated Jun. 26, 2014 (D. Del. Case No. 14-709).
Drug Marketing Approval Document for Aloxi I.V. Drip Infusion Bag 0.75 mg, Japanese Ministry of Health, Labour and Welfare (2012). English-language translation (2012).
Approval of Partial Changes in Drup Marketing Approved Items for Aloxi I.V. Drip Infusion Bag 0.75 mg, Japanese Ministry of Health, Labour and Welfare (2012).
Aurobindo Pharma Ltd. Paragraph IV Letter regarding U.S. Patent No. 8,729,094, dated Jul. 25, 2014 (portions redacted).
Defendants' Responsive Claim Construction Brief regarding U.S. Patent No. 8,598,219, dated Jul. 17, 2014 (D.N. J. 11-3962, consolidated).
Cipla Ltd. Paragraph IV Letter regarding U.S. Patent No. 8,729,094, dated Aug. 6, 2014 (portions redacted).
Teva Pharmaceuticals USA, Inc Paragraph IV Letter regarding U.S. Patent No. 8,729,094, dated Aug. 29, 2014.
Expert Report of Patrick P. DeLuca, Ph.D. with Respect to U.S. Patent No. 8,598,219, dated Aug. 15, 2014 (D.N. J. 11-3962, consolidated).
Expert Report of David G. Frame, Pharm.D. with Respect to U.S. Patent No. 8,598,219, dated Aug. 15, 2014 (D.N. J. 11-3962, consolidated) (confidentiality designation redacted).
Opening Expert Report of John P. Fruehauf, M.D., Ph.D. for U.S. Patent No. 8,598,219, dated Aug. 15, 2014 (D.N. J. 11-3962, consolidated) (confidentiality designation and other portions redacted).
Opening Expert Report of Lee Kirsch, Ph.D. for U.S. Patent No. 8,598,219, dated Aug. 15, 2014 (D.N. J. 11-3962, consolidated) (confidentiality designation and other portions redacted).
Expert Report of Maurie Markman, M.D. with Respect to U.S. Patent No. 8,598,219, dated Aug. 15, 2014 (D. N. J. 11-3962, consolidated) (confidentiality designation and other portions redacted).
Opening Expert Report of Paul Myrdal, Ph.D. for U.S. Patent No. 8,598,219, dated Aug. 15, 2014 (D.N. J. 11-3962, consolidated) (confidentiality designation and other portions redacted).
Second Opening Expert Report of Dr. Bert Spilker with Respect to U.S. Patent No. 8,598,219, dated Aug. 15, 2014 (D.N. J. 11-3962, consolidated) (confidentiality designation and other portions redacted).
K. A. Connors, Introduction to Chemical Kinetics, Chemical Kinetics the Study of Reaction Rates in Solution, John Wiley & Sons, Inc., 1990, Ch. 1, pp. 1-15.
R. G. Strickley, Parenteral formulations of small molecule therapeutics marketed in the United States (1999)—Part I. *PDA J. Pharm. Sci. Technol.* 53:324-349 (1999).
Physicians' Desk Reference, entries for Hespan® (pp. 933-935) and Hyperstat® I.V. Diazoxide Injection (pp. 2848-2849) ($53^{rd}$ ed. 1999).
Physicians' Desk Reference for Astromorph/PF® (pp. 594-595); Baxter's Atrophine Sulfate Injection (p. 858); Baxter's Dobutamine Hydrochloride Injection (p. 861); Duramorph® (p. 863); Baxter's Fentanyl Citrate Injection (p. 868); Baxter's Metoclopramide Injection (p. 871); Baxter's Phenylephrine Hydrochloride Injection (pp. 872-873); Robinul® (p. 873; 2940-42); Phenytoin Sodium Injection (p. 1312); and Diflucar® (pp. 2681-2685) ($56^{th}$ ed. 2002).
The United States Pharmacopeia (USP 26) The National Formulary (NF 21), Official from Jan. 1, 2003, entries for Atrophine Sulfate Injection (p. 192); Diazoxide Injection (p. 591); Dobutamine Hydrochloride Injection (p. 652); Fentanyl Citrate Injection (p. 781); Glycopyrrolate Injection (p. 870); Lidocaine Hydrochloride and Dextrose Injection (pp. 1079-1080); Metoclopramide Injection (pp. 1217-1218); Morphine Sulfate Injection (pp. 1254-1255); Phenylephrine Hydrochloride Injection (pp. 1459-1460); Phenytoin Sodium Injection (pp. 1471-1472); Potassium Chloride for Injection (pp. 1503-1504) (2002).
HELSN0004208 (2002) (redacted).
Full Prescribing Information for Aloxi (palonosetron HCl) Injection for Intravenous Use (2014).
Preformulation Book, Syntex Research, pp. C1-7, C1-19, and C1-26 (1993) (redacted).
Accord Healthcare, Inc.'s Petition for Post Grant Review of U.S. Patent No. 8,598,219 dated Sep. 2, 2014.
Exhibit 1015 to Accord Healthcare, Inc.'s Petition for Post Grant Review of U.S. Patent No. 8,598,219, Declaration of Arnold J. Repta, Ph.D. dated Sep. 2, 2014.
Rebuttal Expert Report of Gordon L. Amidon, Ph.D. concerning U.S. Patent No. 8,598,219, dated Sep. 15, 2014 (D.N. J. 11-3962, consolidated) (confidentiality designation and other portions redacted).
Rebuttal Expert Report of Keith A. Candiotti, M.D. with respect to U.S. Patent No. 8,598,219, dated Sep. 15, 2014 (D.N. J. 11-3962, consolidated) (confidentiality designation and other portions redacted).
Second Rebuttal Expert Report of Carl C. Peck, M.D. dated Sep. 15, 2014 (D.N. J. 11-3962, consolidated) (confidentiality designation and other portions redacted).
Rebuttal Expert Report of Tanios Bekaii-Saab, M.D. with respect to U.S. Patent No. 8,598,219, dated Sep. 15, 2014 (D.N. J. 11-3962, consolidated) (confidentiality designation and other portions redacted).
Answer and Counterclaims of Dr. Reddy's Laboratories, Ltd. and Dr. Reddy's Laboratories, Inc. to Complaint for Patent Infringement regarding U.S. Patent No. U.S. Patent No. 8,729,094 dated Sep. 5, 2014 (D.N. J. Case No. 14-4274).
Dr. Reddy's Laboratories, Ltd.'s and Dr. Reddy's Laboratories, Inc.'s Paragraph IV Letter regarding U.S. Patent Nos. 8,518,981, 8,598,218, 8,598,219, and 8,729,094, dated Sep. 19, 2014 (portions redacted).
Dr. Reddy's Laboratories, Ltd.'s and Dr. Reddy's Laboratories, Inc.'s Paragraph IV Letter regarding U.S. Patent Nos. 8,518,981, 8,598,218, 8,598,219, and 8,729,094, dated Sep. 24, 2014 (portions redacted).
R. M. Eglen and D. W. Bonhaus, "5-Hydroxytryptamine (5-HT)$_3$ Receptors: Molecular Biology, Pharmacology and Therapeutic Importance," Curr Pharm Des. 2:367-74 (1996).
"Helsinn Announces That Patient Enrollment for Phase III Palonosetron Trials Progresses Both in USA and Europe," PR Newswire, Sep. 14, 2000.
G. Piraccini, et al., "A Novel Anti-Emetic Agent, Palonosetron (RS 25259-197): Evidence From Phase I Trials," Support Care Cancer, Jun. 2001, vol. 9, No. 4, Abstract No. P-41 and associated poster presentation.
RS-25259-197, Drugs Fut. 1996, 21(9):906-910 (1996).

(56) References Cited

OTHER PUBLICATIONS

Palonosetron Hydrochloride RS-25259-197, Drugs Fut. 2000, 25(9):982 (Sep. 2000).
Palonosetron Hydrochloride, Drugs Fut. 2001, 26(9):911 (Sep. 2001).
R. E. Leak and J. D. Woodford, "Pharmaceutical Development of Ondansetron Injection," Eur J Cancer Clin Oncol. 25(Suppl 1):567-69 (1989).
Reply Expert Report of David G. Frame, Pharm. D. with respect to U.S. Patent No. 8,598,219 dated Oct. 10, 2014 (D.N. J. 11-3962, consolidated) (confidentiality designations redacted).
Reply Expert Report of Maurie Markman, M.D. with respect to U.S. Patent No. 8,598,219 dated Oct. 10, 2014 (D.N. J. 11-3962, consolidated) (confidentiality designations redacted).
Reply Expert Report of John P. Fruehauf, M.D., Ph.D. for U.S. Patent No. 8,598,219 dated Oct. 10, 2014 (D.N. J. 11-3962, consolidated) (confidentiality designation redacted).
Reply Expert Report of Lee Kirsch, Ph.D. for U.S. Patent No. 8,598,219 dated Oct. 10, 2014 (D.N. J. 11-3962, consolidated) (confidentiality designation redacted).
Reply Expert Report of Paul Myrdal, Ph.D. for U.S. Patent No. 8,598,219 dated Oct. 10, 2014 (D.N. J. 11-3962, consolidated) (confidentiality designation redacted).
Second Reply Expert Report of Dr. Bert Spilker regarding U.S. Patent No. 8,598,219 dated Oct. 10, 2014 (D.N. J. 11-3962, consolidated) (confidentiality designations redacted).
Exela Pharma Sciences LLC's Paragraph IV Letter regarding U.S. Patent Nos. 7,947,724, 7,947,725, 7,960,424, 8,518,981, 8,598,218, 8,598,219, and 8,729,094, dated Oct. 16, 2014 (portions redacted).
Final Joint Claim Construction Chart regarding U.S. Patent Nos. 7,947,724, 7,947,725, 7,960,424, 8,598,219, and 8,729,094 dated Oct. 24, 2014 (D. Del. Case Nos. 13-688 and 14-709).
Mylan Institutional LLC's Opening Claim Construction Brief dated Dec. 5, 2014 (D. Del. Case No. 13-688, consolidated).
Defendants Cipla Ltd. and Cipla USA, Inc.'s Corrected Opening Claim Construction Brief dated Jan. 27, 2015 (D. Del. Case No. 13-688, consolidated).
Plaintiffs' Opening Claim Construction Brief dated Dec. 5, 2014 (D. Del. Case No. 13-688, consolidated).
Defendants Teva Pharmaceuticals USA, Inc. and Teva Pharmaceutical Industries Ltd. Corrected Answer to Complaint for Patent Infringement and Counterclaim for Declaratory Judgment regarding U.S. Patent No. 8,729,094 dated Jan. 8, 2015 (D.N. J. Case No. 14-6341).
Termination of the Proceeding (Case No. PGR2014-00010) dated Nov. 24, 2014.
Declaration of Dr. Neervalur Raghavan, Ph.D. with Exhibits 1-25, dated Sep. 28, 2014.
Gavis Pharma LLC's Paragraph IV Letter regarding U.S. Patent Nos. 7,947,724, 7,947,725, 7,960,424, 8,518,981, 8,598,218, 8,598,219, and 8,729,094, dated Dec. 31, 2014 (portions redacted).
Answer, Defenses, and Counterclaims of Defendants Exela Pharma Sciences, LLC, Exela Pharmsci, Inc. and Exela Holdings, Inc. to Complaint regarding U.S. Patent Nos. 8,518,981 and 8,598,218 redacted version dated Dec. 29, 2014 (D. Del. Case No. 14-1444).
Defendant Mylan Institutional, LLC's Responsive Claim Construction Brief dated Jan. 14, 2015 (D. Del. Case No. 13-688, consolidated).
Defendants Cipla Ltd. and Cipla USA, Inc.'s Corrected Answering Claim Construction Brief dated Jan. 27, 2015 (D. Del. Case No. 13-688, consolidated).
Plaintiffs' Responsive Claim Construction Brief, redacted public version dated Jan. 20, 2015 (D. Del. Case No. 13-688, consolidated).
On Sale and Public Use Bars to Patentability After AIA: Minimizing the Risk of Patent Ineligibility or Invalidation, Cover and Slide 74, Nov. 7, 2013.
Hospira Inc.'s Paragraph IV Letter regarding U.S. Pat. Nos. 7,947,724, 7,947,725, 7,960,424, 8,518,981, 8,598,218, 8,598,219, and 8,729,094, dated Feb. 10, 2015 (portions redacted).
Par Pharmaceutical, Inc.'s Paragraph IV Letter regarding U.S. Patent Nos. 7,947,724, 7,947,725, 7,960,424, 8,518,981, 8,598,218, 8,598,219, and 8,729,094, dated Feb. 10, 2015 (portions redacted).
Dr. Reddy's Laboratories, Ltd.'s and Dr. Reddy's Laboratories, Inc.'s Second Amended Invalidity Contentions Pursuant to L. Pat. R. 3.6(c) dated Mar. 12, 2015 (D.N. J. Nov. 3962, consolidated).

LIQUID PHARMACEUTICAL FORMULATIONS OF PALONOSETRON

This is a continuation of U.S. Ser. No. 13/902,299, filed May 24, 2013, which is a continuation of U.S. Ser. No. 13/901,437, filed May 23, 2013 (now U.S. Pat. No. 8,598, 219), which is a continuation-in-part of U.S. Ser. No. 13/087, 012 filed Apr. 14, 2011 (now U.S. Pat. No. 8,518,981), which is a continuation of U.S. Ser. No. 11/186,311 filed Jul. 21, 2005 (now U.S. Pat. No. 7,947,724), which is a continuation of PCT/EP04/000888, filed Jan. 30, 2004, which claims priority to U.S. Provisional Application 60/444,351, filed Jan. 30, 2003. The content of these applications is incorporated herein by reference.

FIELD OF THE INVENTION

The present invention relates to shelf-life stable liquid formulations of palonosetron that are especially useful in the preparation of injectable and oral medicaments.

BACKGROUND OF THE INVENTION

Emesis is a devastating consequence of cytotoxic therapy, radiotherapy, and post-operative environments that drastically affects the quality of life of people undergoing such treatments. In recent years a class of drugs referred to as 5-$HT_3$ (5-hydroxytryptamine) receptor antagonists has been developed that treat such emesis by antagonizing cerebral functions associated with the 5-$HT_3$ receptor. See *Drugs Acting on 5-Hydroxytryptamine Receptors*: The Lancet Sep. 23, 1989 and references cited therein. Drugs within this class include ondansetron, granisetron, alosetron, tropisetron, and dolasetron. These 5-$HT_3$ antagonists are often administered intravenously shortly before chemotherapy or radiotherapy is initiated, and can be administered more than once during a cycle of chemotherapy or radiotherapy. In addition, they are often supplied as tablets or oral elixirs to either supplement an intravenous administration, or to ease home usage of the drug if the patient is self-administering the chemotherapeutic regimen.

Because some chemotherapeutic agents can induce emesis over extended periods of several days even when they are administered only once, it would be desirable to administer an emesis-inhibiting drug such as a 5-$HT_3$ antagonist every day until the risk of emesis has substantially subsided. The present class of 5-$HT_3$ antagonists has not proven especially helpful meeting this need, however, because the 5-$HT_3$ receptor antagonists currently marketed have proven to be less effective in controlling delayed nausea and vomiting than they are at controlling acute emesis. Sabra, K, *Choice of a 5$HT_3$ Receptor Antagonist for the Hospital Formulary*. EHP, October 1996; 2 (suppl 1):S19-24.

Recently, clinical investigations have been made concerning palonosetron, a new 5-$HT_3$ receptor antagonist reported in U.S. Pat. No. 5,202,333. These investigations have shown that the drug is an order of magnitude more potent than most existing 5-$HT_3$ receptor antagonists, has a surprising half-life of about 40 hours, and is effective to reduce delayed-onset nausea induced by chemotherapeutic agents. However, formulating palonosetron in liquid formulations has not proven an easy task, typically due to shelf-stability issues. U.S. Pat. No. 5,202,333 discloses an intravenous formulation of palonosetron in example 13 that contains the following ingredients:

| Ingredient | Mg |
| --- | --- |
| Palonosetron HCl | 10-100 mg. |
| Dextrose Monohydrate | q.s. to make Isotonic |
| Citric Acid Monohydrate | 1.05 mg. |
| Sodium Hydroxide | 0.18 mg. |
| WFI | To 1.0 ml. |

The formulation has a pH of 3.7 and a shelf stability of less than the 1-2 year time period required by health authorities in various countries.

Ondansetron, its uses, and medicaments made with ondansetron are disclosed in U.S. Pat. Nos. 4,695,578, 4,753, 789, 4,929,632, 5,240,954, 5,344,658, 5,578,628, 5,578,632, 5,922,749, 5,622,720, 5,955,488, and 6,063,802. Commercially it is distributed by GlaxoSmithKline as Zofran® and is indicated for prevention of postoperative nausea and vomiting (PONV), cancer chemotherapy-induced nausea and vomiting (CINV), and radiotherapy-induced nausea and vomiting (RINV) and it is available as an injection, tablets and solution, and as Zofran ODT® (ondansetron) Orally Disintegrating Tablets.

Granisetron, its uses, and medicaments made with granisetron are disclosed in U.S. Pat. Nos. 4,886,808, 4,937,247, 5,034,398 and 6,294,548. Commercially it is distributed by Roche Laboratories Inc. as Kytril®, indicated for the prevention of nausea and vomiting associated with chemotherapy or radiation therapy, and is offered in tablet form, oral solution, and as an injection.

Alosetron, its uses, and medicaments made with alosetron are disclosed in U.S. Pat. Nos. 5,360,800 and 6,284,770. Commercially it is distributed by GlaxoSmithKline as Lotronex®.

Tropisetron is commercially available as Navoban® (Novartis) CAS-89565-68-4 (tropisetron); CAS-105826-92-4 (tropisetron hydrochloride) and it is indicated for treatment of PONV and CINV.

Dolasetron, its uses, and medicaments made with ondansetron are disclosed in U.S. Pat. Nos. 5,011,846, and 4,906,755. Commercially it is distributed by Aventis Pharmaceuticals Inc. as Anzemet®, indicated for prevention of both PONV and CINV, and it is offered in the form of a tablet or an intravenous solution.

Therefore, there exists a need for a palonosetron formulation with increased stability and thereby increased shelf life. There also exists a need for an appropriate range of concentrations for both the 5-$HT_3$ receptor antagonist and its pharmaceutically acceptable carriers that would facilitate making a formulation with this increased stability.

It is an object of the present invention to provide a formulation of Palonosetron hydrochloride with increased pharmaceutical stability for preventing and/or reducing emesis.

It is another object of the invention to provide an acceptable range of concentrations which will stabilize a formulation containing Palonosetron hydrochloride.

It is a further object of the invention to provide a formulation of Palonosetron which would allow for prolonged storage.

It is also an object of the invention to provide a formulation of Palonosetron which would allow terminal sterilization.

SUMMARY OF THE INVENTION

The inventors have made a series of discoveries that support a surprisingly effective and versatile formulation for the treatment and prevention of emesis using palonosetron. These formulations are shelf stable for periods greater than 24 months at room temperature, and thus can be stored without refrigeration, and manufactured using non-aseptic, terminal sterilization processes.

In one aspect, the inventors have discovered that formulations which include the active ingredient palonosetron require in some instances only $\frac{1}{10}^{th}$ the amount of other previously known compounds for treating emesis, which surprisingly allows the use of concentrations of palonosetron far below those that would ordinarily be expected. Thus, in one embodiment the invention provides a pharmaceutically stable solution for preventing or reducing emesis comprising a) from about 0.01 mg/mL to about 5 mg/mL palonosetron or a pharmaceutically acceptable salt thereof; and b) a pharmaceutically acceptable carrier.

The inventors have further discovered that by adjusting the formulation's pH and/or excipient concentrations it is possible to increase the stability of palonosetron formulations. Therefore, in another embodiment, the invention provides a pharmaceutically stable solution for preventing or reducing emesis comprising a) palonosetron or a pharmaceutically acceptable salt thereof; and b) a pharmaceutically acceptable carrier, at a pH from about 4.0 to about 6.0. In another embodiment the invention provides a pharmaceutically stable solution for preventing or reducing emesis comprising from about 0.01 to about 5.0 mg/ml palonosetron or a pharmaceutically acceptable salt thereof; from about 10 to about 100 millimoles citrate buffer; and from about 0.005 to about 1.0 mg/ml EDTA.

The inventors have further discovered that the addition of mannitol and a chelating agent can increase the stability of palonosetron formulations. Therefore, in still another embodiment the invention provides a pharmaceutically stable solution for preventing or reducing emesis comprising a) palonosetron or a pharmaceutically acceptable salt thereof and b) a pharmaceutically acceptable carrier, wherein the pharmaceutically acceptable carrier comprises a chelating agent and mannitol.

DETAILED DESCRIPTION OF THE INVENTION

Definitions

"Vial" means a small glass container sealed with the most suitable stopper and seal, other suitable primary containers may be used, for instance, but not limited to, pre-filled syringes. Vial also means a sealed container of medication that is used one time only, and includes breakable and non-breakable glass vials, breakable plastic vials, miniature screw-top jars, and any other type of container of a size capable of holding only one unit dose of palonosetron (typically about 5 mls.).

Throughout this specification the word "comprise," or variations such as "comprises" or "comprising," will be understood to imply the inclusion of a stated element, integer or step, or group of elements, integers or steps, but not the exclusion of any other element, integer or step, or group of elements, integers or steps "Palonosetron" means (3aS)-2,3,3a,4,5,6-Hexahydro-2-[(S)-1-Azabicyclo[2.2.2]oct-3-yl]2,3,3a,4,5,6-hexahydro-1-oxo-1Hbenz[de]isoquinoline, and is preferably present as the monohydrochloride. Palonosetron monohydrochloride can be represented by the following chemical structure:

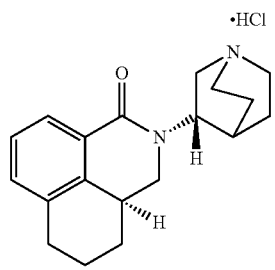

Concentrations—When concentrations of palonosetron are given herein, the concentration is measured in terms of the weight of the free base. Concentrations of all other ingredients are given based on the weight of ingredient added to the solution.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)benzoic acid, cinnamic acid, mandelic acid, methanesulfonic acid, ethanesulfonic acid, 1,2,-ethanedisulfonic acid, 2-hydroxyethanesulfonic acid, benzenesulfonic acid p-chlorobenzenesulfonic acid, 2-naphthalenesulfonic acid, p-toluenesulfonic acid, camphorsulfonicacid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like.

In addition, pharmaceutically acceptable salts may be formed when an acidic proton present is capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

Discussion

The fact that palonosetron can be formulated in some instances at concentrations of only about $\frac{1}{10}^{th}$ the amount of other previously known compounds for treating emesis, surprisingly allows the use of concentrations of palonosetron far below those that would ordinarily be expected. Thus, in one embodiment the invention provides a pharmaceutically stable solution for preventing or reducing emesis comprising a) from about 0.01 mg/mL to about 5 mg/mL palonosetron or a pharmaceutically acceptable salt thereof; and b) a pharmaceutically acceptable carrier. Similarly, in another embodiment the invention provides a method of formulating a pharmaceutically stable solution of palonosetron comprising admixing from about 0.01 mg/mL to about 5 mg/mL palonosetron or a pharmaceutically acceptable salt thereof; with a pharmaceutically acceptable carrier. In alternative embodiments, the formulation includes palonosetron or a pharmaceutically acceptable salt thereof in a concentration from about 0.02 mg/mL to about 1.0 mg/mL, from about 0.03 mg/mL to about 0.2 mg/mL, and most optimally about 0.05 mg/ml.

A particular advantage associated with the lower dosages of intravenous palonosetron is the ability to administer the drug in a single intravenous bolus over a short, discrete time period. This time period generally extends from about 10 to about 60 seconds, or about 10 to about 40 seconds, and most preferably is about 10 to 30 seconds. In one particular embodiment the palonosetron is supplied in vials that comprise 5 ml. of solution, which equates to about 0.25 mg of palonosetron at a concentration of about 0.05 mg/ml.

The inventors have further discovered that by adjusting the formulation's pH and/or excipient concentrations it is possible to increase the stability of palonosetron formulations. Therefore, in another embodiment, the invention provides a pharmaceutically stable solution for preventing or reducing emesis comprising a) palonosetron or a pharmaceutically acceptable salt thereof; and b) a pharmaceutically acceptable carrier, at a pH from about 4.0 to about 6.0. Similarly, in another embodiment the invention provides a method of formulating a pharmaceutically stable solution of palonosetron comprising admixing a) palonosetron or a pharmaceutically acceptable salt thereof; and b) a pharmaceutically acceptable carrier, at a pH from about 4.0 to about 6.0. In alternative embodiments, the pH is from about 4.5 to about 5.5, and most optimally about 5.0. There are many examples to those of skill in the art of suitable solutions to adjust the pH of a formulation. Two exemplary solutions are sodium hydroxide and hydrochloric acid solution, either of which could be used to adjust the pH of the formulation.

In another embodiment the invention provides a pharmaceutically stable solution for preventing or reducing emesis comprising from about 0.01 to about 5.0 mg/ml palonosetron or a pharmaceutically acceptable salt thereof and (i) from about 10 to about 100 millimoles citrate buffer, and/or (ii) from about 0.005 to about 1.0 mg/ml EDTA. Similarly, in another embodiment the invention provides a method of formulating a pharmaceutically stable solution of palonosetron comprising admixing from about 0.01 to about 5.0 mg/ml palonosetron or a pharmaceutically acceptable salt thereof and (i) from about 10 to about 100 millimoles citrate buffer, and/or (ii) from about 0.005 to about 1.0 mg/ml EDTA. The citrate buffer can be in the form of citric acid and/or a salt of citric acid such as trisodium citrate. In various embodiments, the ranges of one or more of the foregoing ingredients can be modified as follows:

The formulation may comprise palonosetron or a pharmaceutically acceptable salt thereof in a concentration from about 0.02 mg/mL to about 1.0 mg/mL, from about 0.03 mg/mL to about 0.2 mg/mL palonosetron hydrochloride, and most optimally about 0.05 mg/ml.

The formulation may comprise citrate buffer in a concentration of from about 10 to about 40 millimoles, or 15-30 millimoles.

The formulation may comprise EDTA in a concentration of from about 0.005 mg/ml to about 1.0 mg/ml, or about 0.3 to about 0.7 mg/ml, and most optimally about 0.5 mg/ml.

The inventors have further discovered that the addition of mannitol and a chelating agent can increase the stability of palonosetron formulations. Therefore, in still another embodiment the invention provides a pharmaceutically stable solution for preventing or reducing emesis comprising a) palonosetron or a pharmaceutically acceptable salt thereof and b) a pharmaceutically acceptable carrier, wherein the pharmaceutically acceptable carrier comprises a chelating agent and mannitol. Similarly, in another embodiment the invention provides a method of formulating a pharmaceutically stable solution of palonosetron comprising admixing a) palonosetron or a pharmaceutically acceptable salt thereof and b) a pharmaceutically acceptable carrier, wherein the pharmaceutically acceptable carrier comprises a chelating agent and mannitol. The chelating agent is preferably EDTA, and, in various embodiments the chelating agent is present in a concentration of from about 0.005 to about 1.0 mg/mL or from about 0.05 mg/mL to about 1.0 mg/mL or from about 0.3 to about 0.7 mg/ml, or most optimally about 0.5 mg/mL. In various embodiments the mannitol is present in a concentration of from about 10.0 mg/ml to about 80.0 mg/ml, from about 20.0 mg/mL to about 60.0 mg/ml, or from about 40.0 to about 45.0 mg/ml.

Injectable formulations are typically formulated as aqueous solutions in which water is the primary excipient. Oral formulations will differ from injectable formulations generally by the additional presence of flavoring agents, coloring agents, or viscosity agents. Natural or synthetic sweeteners include, among others, mannitol, sorbitol, saccharose, saccharine, aspartame, acelsulphame K, or cyclamate. These agents are generally present in concentrations in excess of 100 mg/ml or 250 mg/ml when used as sweetening agents, in contrast to the 41.5 mg/ml concentration of mannitol described in some of the embodiments of the invention, in which mannitol is acting simply as a tonicifying agent.

The formulations of the present invention are particularly suited for use in injectable and oral liquid formulations, but it will be understood that the solutions may have alternative uses. For example, they may be used as intermediates in the preparation of other pharmaceutical dosage forms. Similarly, they may have other routes of administration including intranasal or inhalation. Injectable formulations may take any route including intramuscular, intravenous or subcutaneous.

Still further embodiments relate to improvements in the ease with which the palonosetron formulation can be stored or manufactured. In particular, the inventors have discovered that the formulations of the present invention allow storage of the product for extended periods at room temperature. Thus, in yet another embodiment the invention provides a method of storing one or more containers in which are contained a solution of palonosetron or a pharmaceutically acceptable salt thereof comprising: a) providing a room comprising said one or more containers; b) adjusting or maintaining the temperature of the room at greater than about ten, 15, or 20 degrees celcius; and c) storing said containers in said room for one month, 3 months, 6 months, one year, 18 months, 24 months or more (but preferably not exceeding 36 months), wherein (i) the palonosetron or pharmaceutical salt thereof is present in a concentration of from about 0.01 mg/mL to about 5.0 mg/mL, (ii) the pH of the solution is from about 4.0 to about 6.0, (iii) the solution comprises from about 0.01 to about 5.0 mg/ml palonosetron or a pharmaceutically acceptable salt thereof, from about 10 to about 100 millimoles citrate buffer and from about 0.005 to about 1.0 mg/ml EDTA, (iv) the solution comprises a chelating agent, or (v) the solution comprises from about 10 to about 100 milliMoles of a citrate buffer.

The stability of the foregoing formulations also lends itself well to terminal sterilization processes in the manufacturing process. Therefore, in still another embodiment the invention provides a method of filling a container in which is contained a solution of palonosetron or a pharmaceutically acceptable salt thereof comprising: a) providing one or more sterile open containers (preferably 5 ml. vials); b) filling said containers with a solution of palonosetron in a non-aseptic environment; c) sealing said filled containers; and d) sterilizing said sealed, filled containers, wherein (i) the palonosetron or pharmaceutical salt thereof is present in a concentration of from about 0.01 mg/mL to about 5 mg/mL, (ii) the pH of the solution is from about 4.0 to about 6.0, (iii) the solution comprises from about 0.01 to about 5.0 mg/ml palonosetron or a pharmaceutically acceptable salt thereof, from about 10 to about 100 millimoles citrate buffer and from about 0.005 to about 1.0 mg/ml EDTA, (iv) the solution comprises a chelating agent, or (v) the solution comprises from about 10 to about 100 milliMoles of a citrate buffer.

EXAMPLES

Example 1

Stabilizing pH

A study was conducted to determine the effect of pH on formulations containing palonosetron hydrochloride, measuring the stability at 80° C. at pH 2.0, 5.0, 7.4, and 10.0. The results indicated that palonosetron hydrochloride is most stable at pH 5.0.

Example 2

Stabilizing Concentration Ranges

A formulation optimization study was performed using an experimental design software. Twenty-four lots of drug product were analyzed to investigate the appropriate concentration ranges for palonosetron hydrochloride (0.05 mg/mL to 5.0 mg/mL), citrate buffer (0 to 80 mM) and EDTA (0 to 0.10%). The level of EDTA and citrate buffer were selected based on the optimal formulation, which was shown to be formulated with EDTA 0.05% and 20 mM citrate buffer at pH 5.0. The results of this study indicated that palonosetron concentration was also a critical factor in chemical stability, with greatest stability seen at the lowest palonosetron concentrations.

Example 3

Tonicifying Agent

Formulations of palonosetron hydrochloride in citrate buffer were prepared including either a) sodium chloride or b) mannitol. The palonosetron hydrochloride formulation including mannitol showed superior stability. The optimum level of mannitol required for an isotonic solution was found to be 4.15%.

Example 4

Formulation I

The following is a representative pharmaceutical formulation containing palonosetron that is useful for intravenous formulations, or other liquid formulations of the drug.

| Ingredient | mg/mL |
|---|---|
| Palonosetron Hydrochloride | 0.05* |
| Mannitol | 41.5 |

-continued

| Ingredient | mg/mL |
|---|---|
| EDTA | 0.5 |
| Trisodium citrate | 3.7 |
| Citric acid | 1.56 |
| WFJ | q.s. to 1 ml |
| Sodium hydroxide solution and/or hydrochloric acid solution | pH 5.0 ± 0.5 |

*calculated as a free base

Example 5

Formulation II

The following is a representative pharmaceutical formulation containing palonosetron that is useful for oral formulations, or other liquid formulations of the drug.

| Ingredient | mg/mL |
|---|---|
| Palonosetron Hydrochloride | 0.05* |
| Mannitol | 150 |
| EDTA | 0.5 |
| Trisodium citrate | 3.7 |
| Citric acid | 1.56 |
| WFJ | q.s. to 1 ml |
| Sodium hydroxide solution and/or hydrochloric acid solution | pH 5.0 ± 0.5 |
| Flavoring | q.s. |

*calculated as a free base

Example 6

Stability of Palonosetron without Dexamethasone

The physical and chemical stability of palonosetron HCl was studies in concentrations of 5 µg/mL and 30 µg/mL in 5% dextrose injection, 0.9% sodium chloride injection, 5% dextrose in 0.45% sodium chloride injection, and dextrose 5% in lactated Ringer's injection. The admixtures were evaluated over 14 days at 4° C. in the dark and for 48 hours at 23° C. under fluorescent light.

Test samples of palonosetron HCl were prepared in polyvinyl chloride (PVC) bags of the infusion solutions at concentrations of 5 and 30 µg/mL. Evaluations for physical and chemical stability were performed on samples taken initially and after 1, 3, 5, 7, and 14 days of storage at 4° C. and after 1, 4, 24, and 48 hours at 23° C. Physical stability was assessed using visual observation in normal room light and using a high-intensity monodirectional light beam. In addition, turbidity and particle content were measured electronically. Chemical stability of the drug was evaluated by using a stability-indicating high performance liquid chromatographic (HPLC) analytical technique.

All samples were physically stable throughout the study. The solution remained clear, and little or no change in particulate burden and haze level were found. Additionally, little or no loss of palonosetron HCl occurred in any of the samples at either temperature throughout the entire study period.

Example 7

Stability of Palonosetron with Dexamethasone

The physical and chemical stability of palonosetron HCl 0.25 mg admixed with dexamethasone (as sodium phosphate)

10 mg or 20 mg in 5% dextrose injection or 0.9% sodium chloride injection in polyvinyl chloride (PVC) minibags, and also admixed with dexamethasone (as sodium phosphate) 3.3 mg in 5% dextrose injection or 0.9% sodium chloride injection in polypropylene syringes at 4° C. in the dark for 14 days and at 23° C. exposed to normal laboratory fluorescent light over 48 hours, was studied.

Test samples of palonosetron HCl 5 μg/mL with dexamethasone (as sodium phosphate) 0.2 mg/mL and also 0.4 mg/mL were prepared in polyvinyl chloride (PVC) minibags of each infusion solution. Additionally, palonosetron HCl 25 μg/mL with dexamethasone (as sodium phosphate) 0.33 mg/mL in each infusion solution were prepared as 10 mL of test solution in 20-mL polypropylene syringes. Evaluations for physical and chemical stability were performed on samples taken initially and after 1, 3, 7, and 14 days of storage at 4° C. and after 1, 4, 24, and 48 hours at 23° C. Physical stability was assessed using visual observation in normal room light and using a high-intensity monodirectional light beam. In addition, turbidity and particle content were measured electronically. Chemical stability of the drug was evaluated by using a stability-indicating high performance liquid chromatographic (HPLC) analytical technique.

All samples were physically compatible throughout the study. The solutions remained clear, and little or no change in particulate burden and haze level were found. Additionally, little or no loss of palonosetron HCl and dexamethasone occurred in any of the samples at either temperature throughout the entire study period.

Example 8

Formulation III

The following is a representative pharmaceutical formulation and container closure for palonosetron that is useful for intravenous infusion formulations.

| Ingredient | Amount (mg) |
|---|---|
| Palonosetron Hydrochloride | 0.75[a] |
| Sodium Chloride | 450.0 |
| EDTA | 2.5 |
| Sodium citrate | 18.5 |
| Citric acid monohydrate | 7.8 |
| WFJ | q.s. to 50 mL |
| Sodium hydroxide solution and/or hydrochloric acid solution | pH 4.8 ± 0.5 |
| Container closure system | plastic container[b] plus rubber stopper[c] |

[a] Calculated based on the weight of free base
[b] Polyethylene multilayer film infusion bag.
[c] Isoprene rubber stopper.

This invention has been described with reference to its preferred embodiments. Variations and modifications of the invention will be obvious to those skilled in the art from the foregoing detailed description of the invention.

What is claimed is:

1. A formulation comprising a pharmaceutical sterile aqueous intravenous solution, wherein said pharmaceutical sterile aqueous intravenous solution comprises palonosetron or a pharmaceutically acceptable salt thereof in an amount of 0.25 mg and a concentration of from 0.03 mg/mL to 0.2 mg/mL based on the weight of the palonosetron free base.

2. The formulation of claim 1, wherein said pharmaceutical sterile aqueous intravenous solution has a pH of from 4 to 6.

3. The formulation of claim 1, wherein said pharmaceutical sterile aqueous intravenous solution has a pH of 5.0±0.5.

4. A method of manufacturing a finished container of a pharmaceutical formulation comprising palonosetron or a pharmaceutically acceptable salt thereof, said method comprising: a) providing an open container; b) filling said container with an aqueous intravenous solution comprising said palonosetron or pharmaceutically acceptable salt thereof in an amount of 0.25 mg and a concentration of from 0.03 mg/mL to 0.2 mg/mL based on the weight of the palonosetron free base; c) sealing said filled container; and d) terminally sterilizing said sealed, filled container to obtain said finished container.

5. The method of claim 4, wherein said aqueous intravenous solution has a pH of from 4 to 6.

6. The method of claim 4, wherein said aqueous intravenous solution has a pH of 5.0±0.5.

7. A finished container of palonosetron or a pharmaceutically acceptable salt thereof, manufactured and terminally sterilized by the process of claim 4.

8. The finished container of claim 7, wherein said aqueous intravenous solution has a pH of from 4 to 6.

9. The finished container of claim 7, wherein said aqueous intravenous solution has a pH of 5.0±0.5.

* * * * *